(12) United States Patent
Koblish

(10) Patent No.: US 8,700,120 B2
(45) Date of Patent: *Apr. 15, 2014

(54) MULTI-BEND STEERABLE MAPPING CATHETER

(71) Applicant: Boston Scientific Scimed, Inc., Maple Grove, MN (US)

(72) Inventor: Josef V. Koblish, Sunnyvale, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/864,101

(22) Filed: Apr. 16, 2013

(65) Prior Publication Data

US 2013/0197337 A1 Aug. 1, 2013

Related U.S. Application Data

(63) Continuation of application No. 13/557,038, filed on Jul. 24, 2012, now Pat. No. 8,423,115, which is a continuation of application No. 12/838,285, filed on Jul. 16, 2010, now Pat. No. 8,229,538, which is a continuation of application No. 11/470,132, filed on Sep. 5, 2006, now Pat. No. 7,774,039.

(51) Int. Cl.
*A61B 5/04* (2006.01)

(52) U.S. Cl.
USPC .......................................... 600/374; 600/381

(58) Field of Classification Search
USPC ................................. 600/374, 381
See application file for complete search history.

(56) References Cited

U.S. PATENT DOCUMENTS

| | | | |
|---|---|---|---|
| 4,922,912 | A | 5/1990 | Watanabe |
| 4,940,064 | A | 7/1990 | Desai |
| 5,231,995 | A | 8/1993 | Desai |
| 5,254,088 | A | 10/1993 | Lundquist et al. |
| 5,273,535 | A | 12/1993 | Edwards et al. |

(Continued)

FOREIGN PATENT DOCUMENTS

| | | |
|---|---|---|
| EP | 0842673 A1 | 5/1998 |
| EP | 1005838 A1 | 6/2000 |

(Continued)

OTHER PUBLICATIONS

PCT International Search Report for PCT/US2007/077496, Applicant: Boston Scientific Scimed, Inc., Forms PCT/ISA/210 and 220, dated May 7, 2008.

(Continued)

*Primary Examiner* — Lee S Cohen
(74) *Attorney, Agent, or Firm* — Seager, Tufte & Wickhem, LLC

(57) ABSTRACT

An electrophysiology catheter introduced through the groin and inferior vena cava into the right side of the heart comprises an elongate flexible shaft having a steerable distal section and a prolapsing section located proximally of the distal section. The distal section is inserted into the coronary sinus and a back-steering force is applied to the catheter to anchor the distal section therein, after which the catheter is further advanced to prolapse the prolapsing section against the high right atrium. Electrical pathways in both the coronary sinus and the high right atrium are mapped using respective electrode pairs carried on the distal and prolapsing sections of the catheter.

20 Claims, 3 Drawing Sheets

(56) References Cited

U.S. PATENT DOCUMENTS

| | | | |
|---|---|---|---|
| 5,275,162 | A | 1/1994 | Edwards et al. |
| 5,354,297 | A | 10/1994 | Avitall |
| 5,462,544 | A | 10/1995 | Saksena et al. |
| 5,562,619 | A | 10/1996 | Mirarchi et al. |
| 5,651,786 | A | 7/1997 | Abela et al. |
| 5,687,723 | A | 11/1997 | Avitall |
| 5,730,127 | A | 3/1998 | Avitall |
| 5,785,706 | A | 7/1998 | Bednarek |
| 5,824,005 | A | 10/1998 | Motamedi et al. |
| 5,827,278 | A | 10/1998 | Webster, Jr. |
| 5,865,800 | A | 2/1999 | Mirarchi et al. |
| 5,921,924 | A | 7/1999 | Avitall |
| 5,964,757 | A | 10/1999 | Ponzi |
| 6,002,955 | A | 12/1999 | Willems et al. |
| 6,083,222 | A | 7/2000 | Kleins et al. |
| 6,141,576 | A | 10/2000 | Littmann et al. |
| 6,144,870 | A | 11/2000 | Griffin, III |
| 6,210,362 | B1 | 4/2001 | Ponzi |
| 6,308,090 | B1 | 10/2001 | Tu et al. |
| 6,413,234 | B1 | 7/2002 | Thompson et al. |
| 6,430,426 | B2 | 8/2002 | Avitall |
| 6,716,207 | B2 | 4/2004 | Farnholtz |
| 6,746,446 | B1 | 6/2004 | Hill, III et al. |
| 6,866,662 | B2 | 3/2005 | Fuimaono et al. |
| 6,869,414 | B2 | 3/2005 | Simpson et al. |
| 6,926,669 | B1 | 8/2005 | Stewart et al. |
| 6,987,996 | B2 | 1/2006 | Fuimaono et al. |
| 7,013,170 | B2 | 3/2006 | Bowe |
| 7,081,114 | B2 | 7/2006 | Rashidi |
| 7,089,063 | B2 | 8/2006 | Lesh et al. |
| 7,412,273 | B2 | 8/2008 | Jais et al. |
| 7,419,477 | B2 | 9/2008 | Simpson et al. |
| 7,496,394 | B2 | 2/2009 | Ahmed et al. |
| 7,706,894 | B2 | 4/2010 | Stewart et al. |
| 7,774,039 | B2 | 8/2010 | Koblish |
| 8,229,538 | B2 | 7/2012 | Koblish |
| 8,423,115 | B2 * | 4/2013 | Koblish ............ 600/374 |
| 2003/0009095 | A1 | 1/2003 | Skarda |
| 2008/0086047 | A1 | 4/2008 | McDaniel et al. |

FOREIGN PATENT DOCUMENTS

| | | |
|---|---|---|
| EP | 1502542 A1 | 2/2005 |
| EP | 1532999 A2 | 5/2005 |
| WO | 9510318 A1 | 4/1995 |

OTHER PUBLICATIONS

PCT Written Opinion of the International Search Authority for PCT/US2007/077496, Applicant: Boston Scientific Scimend, Inc., From PCT/ISA/237, dated May 7, 2008.

* cited by examiner

SECTION A-A

SECTION B-B

SECTION C-C

MULTI-BEND STEERABLE MAPPING CATHETER

RELATED APPLICATION DATA

The present application is a continuation of U.S. patent application Ser. No. 13/557,038, filed Jul. 24, 2012, now U.S. Pat. No. 8,423,115; which is a continuation of U.S. patent application Ser. No. 12/838,285, filed Jul. 16, 2010, now U.S. Pat. No. 8,229,538; which is a continuation of U.S. patent application Ser. No. 11/470,132, now U.S. Pat. No. 7,774,039, the entire disclosures are incorporated herein by reference.

FIELD OF INVENTION

This invention pertains to electrophysiology ("EP") mapping catheters and, more particularly, to a multi-bend, steerable catheter configured for accessing and mapping the high right atrium and coronary sinus via groin access and the superior vena cava.

BACKGROUND

Electrophysiology is the study of electrical impulses through the heart and is focused primarily on diagnosing and treating arrhythmias, conditions in which electrical impulses within the heart vary from the normal rate or rhythm of a heartbeat. The most common arrhythmia is atrial fibrillation (AF), which is characterized by rapid, disorganized contractions of the heart's upper chambers, the atria. AF results from abnormal electrical impulses propagating through aberrant myocardial tissue pathways, which leads to ineffective pumping of the blood through the heart, as well as other complications. Atria flutter (AFL), another type of arrhythmia, is characterized by a rapid beating of the atria. Unlike AF, AFL arises from a single electrical wave that circulates rapidly throughout the right side of the heart. Since this arrhythmia can arise from multiple electrical sites, effective treatment requires electrical isolation of the aberrant signal sites, thereby forcing the heart's normal conduction pathway to take over.

The practice of interventional electrophysiology for treating arrhythmias, such as AF and AFL, generally involves inserting specialized catheters into a patient's vasculature and navigating the distal (or "working") end of the catheters into the patient's heart chambers to identify (or "map") the locations of heart tissue that are a source of the arrhythmias. The mapping of the heart's electrical activity is typically accomplished using one or more pairs of electrodes, each pair spaced apart axially along the working end of the catheter. Following or in conjunction with the mapping procedure, the attending physician may use an ablation catheter to disable (or "ablate") the tissue containing the aberrant signal(s) or signal pathway(s), thereby restoring the heart to its normal rhythm.

While catheters may be provided with combined mapping and ablation functionalities, separate mapping and ablation catheters are more typically used, which allows for much greater capability of their respective functions. For example, electrical activity is normally mapped using much smaller electrodes (in surface area) than are used for performing ablation procedures. Because there is significantly less current transmitted through a mapping electrode circuit than through an ablation circuit, the lead wires that connect the mapping electrodes to processing circuitry (e.g., via a pin connector in the catheter handle) are much smaller than are used to couple ablation electrodes to an RF generator. As such, a much greater number of electrodes may be provided on a mapping catheter than on an ablation catheter having a same or similar profile.

For AFL mapping procedures (as well as for some AF procedures), it is important to map the electrical activity in both the coronary sinus (CS) and the right atrium (RA), especially the region of the high right atrium (HRA). Currently, to map both the CS and the RA, a pre-shaped, non-steerable, mapping catheter having two sets of electrodes is inserted through a jugular vein at the base of the patient's neck, through the superior vena cava (SVC), and into the RA, where it bends (or "banks") off of the lower portion of the atrial chamber (i.e., over the isthmus region) and into the CS. While functional for mapping the respective RA and CS, this type of catheter has certain drawbacks. For example, because it passes across the lower atrial chamber, maneuvering the mapping catheter for achieving proper electrical contact in the HRA can be difficult. Further, since most ablation catheters used for AFL and AF interventional procedures are inserted through the groin and inferior vena cava (IVC), and are maneuvered to ablate tissue in the isthmus region of the lower atrial chamber, the mapping catheter extending across the isthmus can block and interfere with the ablation catheter. Plus, the patient and attending physician must cope with having two different access ports into the patient's venous system (i.e., both through the jugular and through the groin), making simultaneous control of the respective mapping and ablation catheters more difficult, and increasing the chances of related complications and patient discomfort.

While there are diagnostic catheters available for mapping the RA and HRA through groin access and the IVC, these typically form a complete distal end loop that encircles the atrial chamber, with a small tail segment for slight penetration into the ostium of the CS. The loop portion extends over the isthmus region in the lower right atrium (LRA), interfering with the ablation catheter, and the limited penetration of the CS results in corresponding limited CS mapping data.

Thus, it would be desirable to provide a diagnostic catheter that may be better positioned for mapping both the HRA and the CS, which is inserted through the groin and IVC, without blocking the isthmus.

SUMMARY OF THE INVENTION

In accordance with one embodiment, an electrophysiology catheter includes an elongate flexible shaft having a steerable distal section and a prolapsing section located proximally of the distal section. A first set of electrodes are carried on the steerable distal section, and a second set of electrodes are carried on the prolapsing section. By way of example, the electrophysiology catheter may be a diagnostic catheter, with the first and second sets of electrodes comprising respective first and second sets of mapping electrode pairs.

The catheter shaft comprising a soft outer tubing that has an embedded reinforcing braid extending from the handle through a main body section of the catheter to increase its hardness. The reinforcing braid terminates in a transition region between the main body section and the prolapsing section, so that the outer shaft of the prolapsing section is much softer, facilitating its prolapsing against the HRA. The distal section may be steered bi-directionally by actuating pull wires (e.g., using a steering mechanism in the catheter handle) having distal ends attached to opposing sides of a flat, resilient center support member positioned in an interior of the distal section. The steering assembly also includes a tightly wound, highly flexible compression coil that extends from the handle to the support member through a central lumen of the outer shaft, with the pull wires positioned within an inner lumen of the flexible coil. To facilitate prolapsing of, and provide structural support to, the prolapsing section, the cross-section of the compression coil changes from generally circular to generally oval or "flattened" within the prolapsing section, prior to the transition to the distal section.

In accordance with another embodiment, a method of mapping conductive pathways in a patient's heart tissue includes the steps of (i) inserting an elongate flexible catheter through an access location proximate the patent's groin and into a patient's venous system, (ii) advancing the catheter through the patient's inferior vena cava and into the right atrium, (iii) directing a steerable distal section of the catheter into the coronary sinus, and (iv) further advancing the catheter to cause a prolapsing section thereof located proximally of the distal section to prolapse against the high right atrium. The method may further include one or more of (v) applying a back-steering force to anchor the distal section in the coronary sinus prior to further advancing the catheter to cause the prolapsing section to prolapse against the HRA wall, (vi) mapping electrical pathways in the patient's coronary sinus using one or more electrode pairs carried on the distal section, and (vii) mapping electrical pathways in the patient's high right atrium using one or more electrode pairs carried on the prolapsing section.

Other and further features and advantages of embodiments of the invention will become apparent from the following detailed description, when read in view of the accompanying figures.

BRIEF DESCRIPTION OF THE DRAWINGS

Embodiments of the invention are illustrated by way of example and not limitation in the figures of the accompanying drawings, in which like references indicate similar elements, and in which.

DETAILED DESCRIPTION

Figure 1:
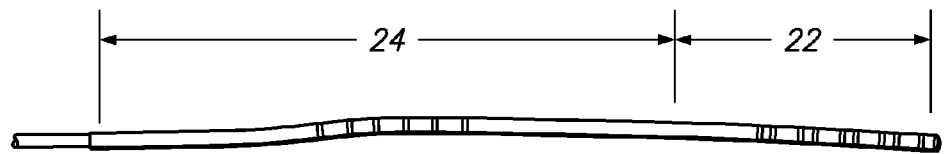
FIG. 1 is a perspective image of a distal end portion of a diagnostic mapping catheter constructed according to one embodiment.
Figure 3:
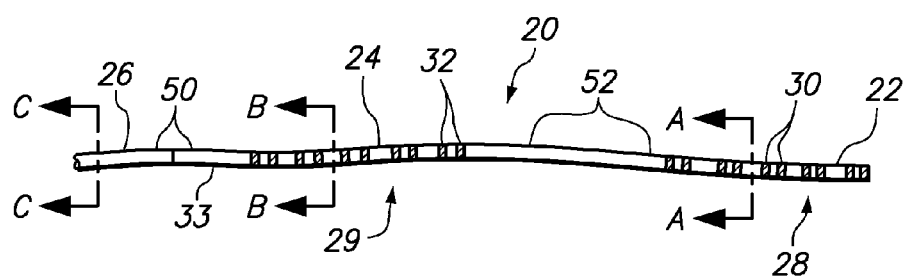
FIG. 3 is a schematic image of the catheter of FIG. 1.

FIG. 1 depicts a distal portion of a diagnostic catheter 20 constructed in accordance with one embodiment of the invention. The catheter 20 comprises an elongate, flexible shaft 21 extending from a proximal handle (not shown), as is well-known in the art for electrophysiology catheters. The catheter shaft 21 generally includes a steerable distal section 22, and a prolapsing section 24 located immediately proximal of the distal section 20, which distal and prolapsing sections 22 and 24 are sized and configured for placement in a patient's coronary sinus (CS) and high right atrium (HRA), respectively. As best seen in FIG. 3, the catheter 20 is a "twenty pole" catheter, with ten electrodes 28 (comprising five electrode pairs 30) carried on the steerable distal section 22 for mapping in the CS, and another ten electrodes 29 (comprising five electrode pairs 32) carried on the prolapsing section 24 for mapping the HRA. The electrodes 28, 29 are coupled to respective lead wires that extend through the interior of the catheter shaft and are preferably bundled together (reference no. 36 in FIGS. 3A-3B) in a well-known manner.

Figure 2:
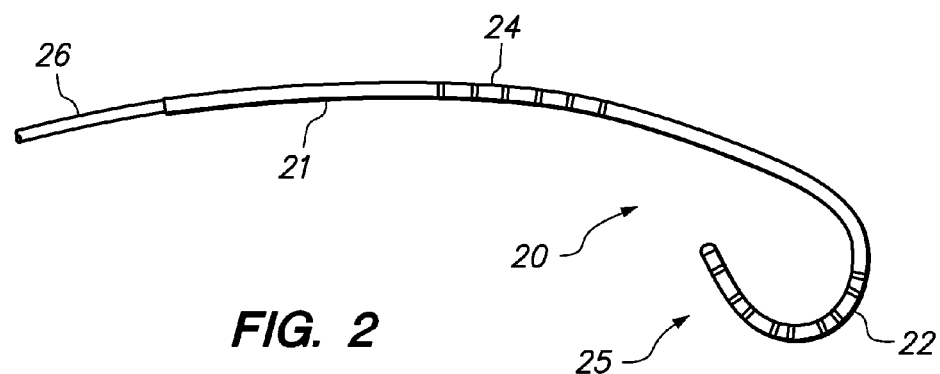
FIG. 2 is a perspective image of the catheter of FIG. 1 with an internal distal steering support member being deflected to form a curved loop segment out of the catheter distal end.
Figure 4:
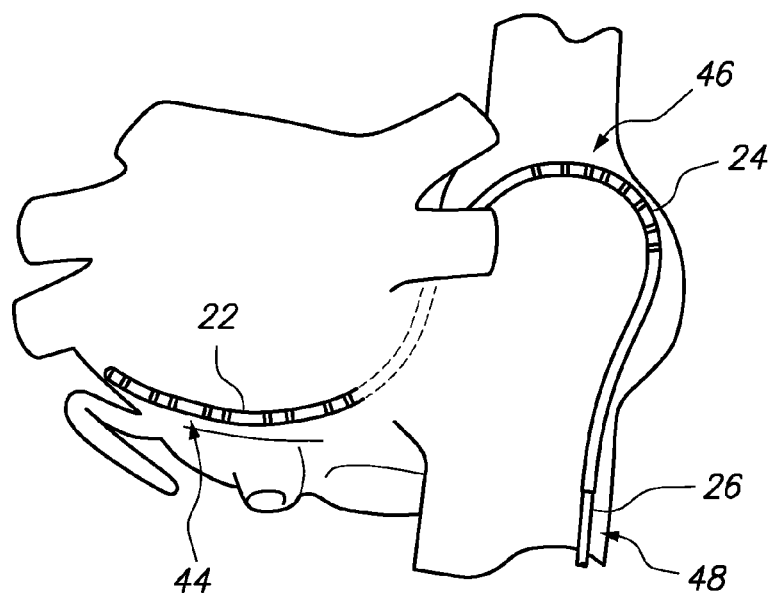
FIG. 4 is a perspective view of the catheter of FIG. 1 extending through the respective inferior vena cava and right atrium, and into the coronary sinus of a three dimensional model of a human heart, with a prolapsed section of the catheter shown slightly torqued and leveraged against the wall of the high right atrium.
Figure 5:
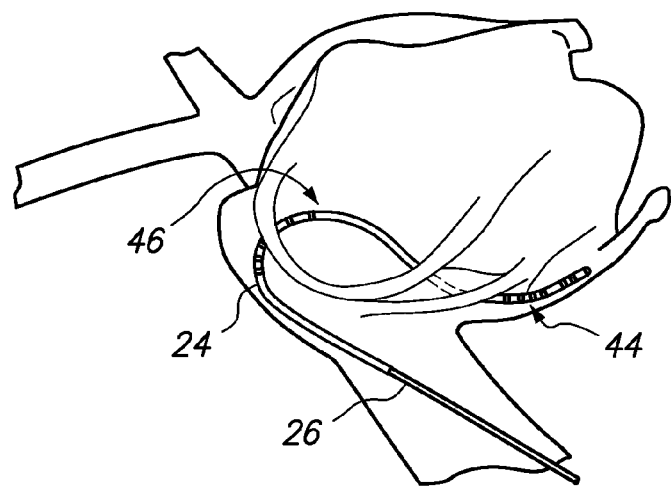
FIG. 5 and FIG. 6 are additional perspective views of the catheter positioned in the heart model of FIG. 4.
Figure 6:
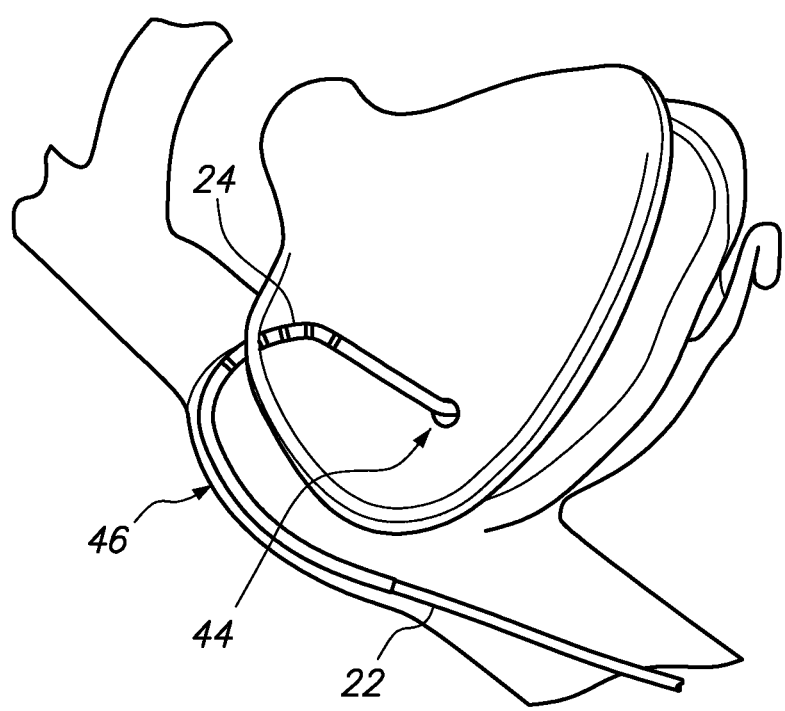

In accordance with one aspect of the invention, the catheter shaft 21 is sized and configured for accessing the venous system through the patient's groin, and for navigation up the inferior vena cava (IVC) (reference no. 48 in FIGS. 4-6) and into the right atrium. Using a standard bi-directional steering support member embedded in the distal section 22 (described below in greater detail), the distal section 22 is guided into the CS. By way of illustration, FIG. 2 shows the distal section 22 of the catheter shaft 21 formed into a three-quarter loop 25 by tensioning of the steering member. As seen in FIGS. 4-6, once the catheter distal section 22 is positioned in the CS 44, the physician applies a "back steering" force on the steering mechanism so that the distal section 22 will become anchored in the CS 44. The catheter 20 is then pushed forward by the physician to cause the prolapsing section 24 to "prolapse" in an arching loop lying against the wall of the HRA 46. It will be appreciated that the prolapsing section 24 is slightly torqued (best seen in FIG. 6) as the distal section 22 positioned in the CS is not in the same plane as the prolapsing section 24 lying across the HRA wall, which provides a more stable positioning of the prolapsing section 24.

Figure 3A:
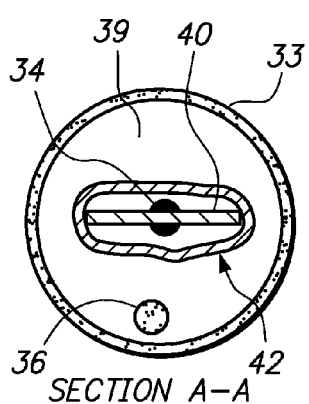
FIG. 3A is a cross-sectional end view taken along dashed line A-A in FIG. 3.
Figure 3B:
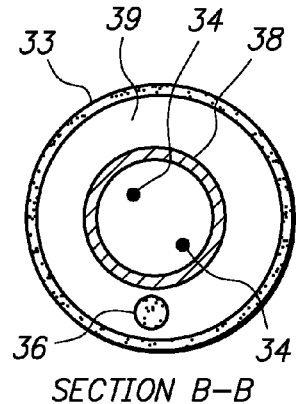
FIG. 3B is a cross-sectional end view taken along dashed line B-B in FIG. 3.
Figure 3C:
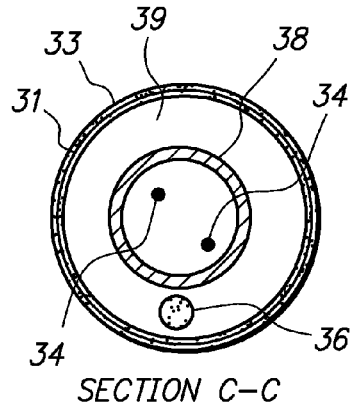
FIG. 3C is a cross-sectional end view taken along dashed line C-C in FIG. 3.

With reference to FIGS. 3, 3A, 3B, and 3C, the steering assembly includes a flat, resilient center support member 40 positioned in an interior of the catheter distal section 22. The support member may be actuated using a well-known steering mechanism (not shown) in the handle by a pair of pull wires 34 having distal ends secured on opposing sides of the steering member 40. As seen in FIG. 3A, a "flattened" Kevlar-reinforced tube 42 is used to constrain the steering wires 34 against the center support member 40.

By way of non-limiting example, the steering assembly in the diagnostic catheter 20 may be similar or identical that used in the Blazer catheter manufactured and distributed by Boston Scientific (www.bostonscientific.com).

The catheter shaft 21 comprises a relatively soft outer tubing 33 with an embedded braid 31 extending through the main body section 26. The braid 31 terminates in a transition region 50 between the main body section 26 and the prolapsing section 24, so that the outer tubing 33 of the shaft 21 in the prolapsing section 24 is relatively soft (e.g., with a hardness of approximately 35 D in one embodiment) compared to shaft of the main body section 26 (e.g., with a hardness of approximately 72 D in one embodiment). The relatively soft outer shaft enables the prolapsing section 24 to readily prolapse into the HRA when the distal section is anchored in the CS. The stiffer outer shaft 33 of the main body section 26 also facilitates prolapsing of the prolapsing section 24 against the HRA wall.

A cross section of the prolapsed section 24 is preferably substantially circular about its outer diameter. Residing in an interior lumen 39 of the outer tube 33 is a tightly wound, flexible compression coil 38 that constitutes part of the steering assembly. The coil 38 also provides a highly flexible structure for facilitating prolapsing of the prolapsing section 24 into (and against the wall of) the HRA. The coil 38 may be made of a stainless steel and preferably extends throughout the catheter body 21, i.e., from the handle to the center support member 40 in the distal section 22. The cross-section of the coil 38 preferably changes from a substantially circular shape in the main body section 26 to a substantially oval or flattened shape in the transition region 50 between the main body and prolapsing sections 26 and 24 in order provide directionality and enhanced torque of the prolapsing section 24. A hinge joint (not shown) may optionally be built into a transition region 52 located between the prolapsing section 24 and distal section 22, to further facilitate prolapsing of the prolapsing section 24 against the wall of the HRA.

It will be appreciated that the diagnostic catheter 20 will typically be used in conjunction with AFL ablation procedures in order to access bi-directional block across the isthmus, without interfering with the ablation catheter during the creation of an isthmus lesion. The catheter 20 may also be used for AF procedures, where it is important for the physician to map the electrical activity in the CS as well as the HRA. Because the catheter 20 is positioned through groin access and the IVC, and in particular because the prolapsing section 24 is torqued against the wall of the HRA, maneuvering for achieving solid electrical contact on the wall of the HRA is much easier than in previously existing RA mapping catheters.

The forgoing illustrated and described embodiments of the invention are susceptible to various modifications and alternative forms, and it should be understood that the invention generally, as well as the specific embodiments described herein, are not limited to the particular forms or methods disclosed, but to the contrary cover all modifications, equivalents and alternatives falling within the scope of the appended claims.

What is claimed is:

1. An electrophysiology catheter, comprising:
   an elongate flexible shaft defining an inner lumen and having a steerable distal section, a prolapsing section located proximally of the distal section, and a main body section located proximally of the prolapsing section;
   a first plurality of electrodes carried on the steerable distal section;
   a second plurality of electrodes carried on the prolapsing section; and
   a flexible inner compression coil extending through the inner lumen of the flexible shaft, wherein a distal portion of the compression coil extends at least partially through the prolapsing section, wherein a cross-sectional shape of the compression coil changes from substantially circular in the main body section to substantially oval or flattened in prolapsing section.

2. The catheter of claim 1, wherein the catheter is a diagnostic catheter, and wherein the first and second pluralities of electrodes each comprise respective mapping electrode pairs.

3. The catheter of claim 1, further comprising a resilient center support member positioned in an interior of the distal section.

4. The catheter of claim 1, wherein the elongate shaft comprises a reinforcing braid embedded therein.

5. The catheter of claim 4, wherein the elongate flexible shaft has a transition region between the main body section and the prolapsing section, wherein the embedded braid terminates in the transition region and the inner compression coil extends through the transition region.

6. The catheter of claim 1, wherein the compression coil extends through the prolapsing section into the steerable distal section.

7. The catheter of claim 1, wherein the second plurality of electrodes overlies the compression coil.

8. The catheter of claim 1, further comprising a plurality of steering wires disposed in a lumen of the compression coil, wherein the compression coil constrains the steering wires radially in the prolapsing section.

9. The catheter of claim 1, further comprising a hinge joint located between the prolapsing section and the steerable distal section.

10. The catheter of claim 9, wherein the prolapsing section is configured to prolapse in a prolapse plane that is different from a plane of the distal section when the distal section is positioned in a patient's coronary sinus.

11. The catheter of claim 10, wherein the hinge joint is configured to bend in the prolapse plane.

12. A method of mapping conductive pathways in a patient's heart tissue using the catheter of claim 10, comprising:
    inserting the catheter through an access location in or proximate to the patient's groin and into the patient's venous system;
    advancing the catheter through the patient's inferior vena cava and into the patient's right atrium;
    directing the steerable distal section into the patient's coronary sinus; and
    further advancing the catheter to cause the prolapsing section to prolapse in the prolapse plane against the patient's high right atrium and to cause the hinge joint to bend in the prolapse plane.

13. A method of mapping conductive pathways in a patient's heart tissue using the catheter of claim 1, comprising:
    inserting the catheter through an access location in or proximate to the patient's groin and into the patient's venous system;
    advancing the catheter through the patient's inferior vena cava and into the patient's right atrium;
    directing the steerable distal section into the patient's coronary sinus; and
    further advancing the catheter to cause the prolapsing section to prolapse against the patient's high right atrium.

14. The method of claim 13, further comprising applying a back-steering force to the catheter to thereby anchor the distal section in the coronary sinus prior to prolapsing the prolapsing section against the high right atrium.

15. The method of claim 13, further comprising mapping electrical pathways in the coronary sinus using at least one pair of the first plurality of electrodes.

16. The method of claim 13, further comprising mapping electrical pathways in the high right atrium using at least one pair of the second plurality of electrodes.

17. A diagnostic mapping catheter, comprising:
    an elongate flexible shaft defining an inner lumen and having a steerable distal section, a prolapsing section located proximally of the distal section, and a main body section located proximally of the prolapsing section, with a reinforcing braid embedded in the shaft of the main body section, wherein the distal section of the shaft may be steered bi-directionally about a resilient center support member positioned in an interior of the distal section;
    a flexible inner compression coil extending through the inner lumen of the shaft, with a distal portion of the compression coil extending at least partially through the prolapsing section, wherein a cross-sectional shape of the compression coil changes from substantially circular in the main body section to substantially oval or flattened in prolapsing section;

a transition region between the main body section and the prolapsing section in which the embedded braid terminates, and through which the inner coil extends;

a first plurality of electrode pairs carried on the distal section; and a second plurality of electrode pairs carried on the prolapsing section.

18. The catheter of claim 17, wherein the compression coil extends through the prolapsing section into the steerable distal section.

19. The catheter of claim 17, wherein the second plurality of electrodes overlies the compression coil.

20. The catheter of claim 17, further comprising a plurality of steering wires disposed in a lumen of the compression coil, wherein the compression coil constrains the steering wires radially in the prolapsing section.

* * * * *

UNITED STATES PATENT AND TRADEMARK OFFICE
CERTIFICATE OF CORRECTION

PATENT NO.        : 8,700,120 B2                                              Page 1 of 1
APPLICATION NO.   : 13/864101
DATED             : April 15, 2014
INVENTOR(S)       : Josef V. Koblish It is certified that error appears in the above-identified patent and that said Letters Patent is hereby corrected as shown below:

In the Specification

Column 1
Line 35: delete "Atria" and insert therefor --Atrial--.

Signed and Sealed this
Twenty-second Day of July, 2014

Michelle K. Lee
*Deputy Director of the United States Patent and Trademark Office*